US006815161B1

(12) United States Patent
Vojdani

(10) Patent No.: US 6,815,161 B1
(45) Date of Patent: *Nov. 9, 2004

(54) DETECTION OF MYCOPLASMA IN PATIENTS WITH CHRONIC FATIGUE SYNDROME AND RELATED DISORDERS

(75) Inventor: Aristo Vojdani, Los Angeles, CA (US)

(73) Assignee: Immunosciences Lab, Inc., Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/283,655

(22) Filed: Apr. 1, 1999

(51) Int. Cl.$^7$ .......................... C07H 21/04; C12Q 1/68
(52) U.S. Cl. ...................... 435/6; 435/91.2; 536/24.3; 536/24.32; 536/24.33
(58) Field of Search ........................... 536/24.32, 24.3, 536/24.33; 435/6, 91.2

(56) References Cited

U.S. PATENT DOCUMENTS

| | | | |
|---|---|---|---|
| 5,627,275 A | 5/1997 | Roll | 236/23.7 |
| 5,766,859 A | 6/1998 | Vojdani et al. | 435/7.1 |
| 5,766,690 A | 7/1998 | Vojdani et al. | 435/6 |
| 5,830,668 A | 11/1998 | Mordechai et al. | 435/7.4 |
| 5,853,996 A | 12/1998 | Mordechai et al. | 435/6 |

OTHER PUBLICATIONS

Nicolson et al. International Journal of Occupational Medicine, Immunology, and Toxicology, vol. 5, No. 1, 1996. p. 69–78.
Nicolson et al. Biomedical Therapy. vol. XVI, No. 4, oct. 1998, p. 266–271.
Ginsburg et al. Arthritis and Rheumatism, vol. 35, No. 4 (Apr. 1992). p. 429–433.
Nicolson et al. International Journal of Medicine, 1998; 1:80–92.
Bej, et al., Multiplex PCR amplification and immobilized capture probes for detection of bacterial pathogens and indicators in water, *Mol. Cell. Probes* 4:353–365, (1990).
Buchwald, et al., Comparison of Patients With Chronic Fatigue Syndrome, Fibromyalgia, and Multiple Chemical Sensitivities, *Arch. Intern. Med* 154:2049–2053 (1994).
Choppa, et al., Multiplex PCR for the detection of *Mycoplasma fermentans, M. hominis* and *M. penetrans* in cell cultures and blood samples of patients with chronic fatigue syndrome, *Mol. Cell. Probes* 12:301–308 (1998).
Fukuda, et al., The Chronic Fatigue Syndrome: A Comprehensive Approach to Its Definition and Study, *Fed. Pract.* 121:953–959 (1994).
Grau, et al., Development of PCR–based assays for the detection of two human mollicute species, *Mycoplasma penetrans* and *M. hominis, Mol. Cell. Probes* 8:139–148 (1994).

Hawkins, et al., Association of Mycoplasma and Human Immunodeficiency virus Infection: Detction of Amplifierd *Mycoplasma fermentans* DNA in Blood, *J. Infect. Dis.* 165:581–585 (1992).
Hayes, et al., Pathogenicity of *Mycoplasma fermentans* and *Mycoplasma penetrans* in Experimentally Infected Chicken Embryos, *Infect. Immun.* 64(8):3419–3424 (1996).
Hopert, et al., Specifity and sensitivity of polymerase chain reaction (PCR) in comparison with other methods for the detection of *mycoplasma* contamination in cell lines, *J. Immunol. Meth.* 164:91–100 (1993).
Kulski, et al., Use of a Multiplex PCR To Detect and Identify *Mycobacterium avium* and M. intracellular in Blood Culture Fluids of AIDS Patients, *J. Cline. Microbial.* 33(3):668–674 (1995).
Montagnier et al., Mycoplasmas as Cofactors in Infection Due to the Human Immunodeficiency Virus, *Clin. Infect. Dis.* 17(Suppl. 1):S309–315 (1993).
Razin, Shmuel, DNA probes and PCR in diagnosis of mycoplasma infections, *Mol. Cell. Probes* 8:497–511 (1994).
Schaeverbeke, et al., Systematic Detection of Mycoplasmas by Culture and Polymerase Chain Reaction (PCR) Procedures in 209 Synovial Fluid Samples, *Br. J. Rheumatol.* 36:310–314 (1997).
Straus, Stephen., History of Chronic Fatigue Syndrome, *Rev. Infect. Dis.* 13(Suppl. 1)S2–S7 (1991).
van Kuppeveld, et al., Detection of Mycoplasma Contamination in Cell Cultures by a Mycoplasma Group–Specific PCR, *Appl. Environ. Microbiol.* 60:149–152 (1994).
van Kuppeveld, et al., Genus– and Species–Specific Identification of Mycoplasmas by 16S rRNA Amplification, *Appl. Environ. Microbiol.* 58:2606–2615 (1992).
Wang, et al., Multiplex PCR for avian pathogenic mycoplasmas, *Mol. Cell Probes* 11:211–216 (1997).
Vojdani, et al. Detection of Mycoplasma genus and *Mycoplasma fermentans* by PCR in patients with Chronic Fatigue Syndrome, *FEMS Immunol. and Med. Microbiol.* 22:355–365 (1998).
Ziem, et al., Chronic Fatigue, Fibromyalgia, and Chemical Sensitivity: Overlapping Disorders, *Arch. Intern. Med.* 154:1913 (1995).

*Primary Examiner*—Jeffrey Fredman
*Assistant Examiner*—Juliet C. Einsmann
(74) *Attorney, Agent, or Firm*—Knobbe, Martens, Olson & Bear, LLP

(57) ABSTRACT

A method for determining an increased likelihood of the presence of chronic fatigue syndrome (CFS), fibromyalgia (FMS), or rheumatoid arthritis (RA) in an individual, comprising isolating blood cells from the individual and determining the presence of one or more *Mycoplasma* species present in the blood cells, wherein the presence of one or more *Mycoplasma* species indicates an increased likelihood of the presence of CFS, FMS, RA or GWS.

27 Claims, 2 Drawing Sheets

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 1
gggagcaaac aggattagat accct                                    25

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 2
tgcaccatct gtcactctgt taacctc                                  27

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide primer -continued

```
<400> SEQUENCE: 3
ggactattgt ctaaacaatt tccc                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 4
ggttattcga tttctaaatc gcct                                              24

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 5
atacatgcat gtcgagcgag                                                   20

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 6
catcttttag tggcgcctta c                                                 21

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 7
catgcaagtc ggacgaagca                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
agcatttcct cttcttacaa                                                   20
```

DETECTION OF MYCOPLASMA IN PATIENTS WITH CHRONIC FATIGUE SYNDROME AND RELATED DISORDERS

BACKGROUND OF THE INVENTION

1. Field of the Invention

The present invention relates to detection of at least one *Mycoplasma* species, including *Mycoplasma fermentans*, *Mycoplasma hominis* and *Mycoplasma penetrans*, in blood samples of patients with chronic fatigue syndrome, fibromyalgia and rheumatoid arthritis.

2. Description of the Related Art

Chronic Fatigue Syndrome (CFS) is an illness with increasingly reported frequency in the United States and other industrialized countries (Straus, *Rev. Infect. Dis.* 13(Suppl. 1):S2–S7, 1991). CFS is characterized by prolonged and debilitating fatigue with multiple non-specific symptoms such as headaches, recurring sore throats, muscle and joint pains and cognitive complaints. Profound fatigue, the hallmark of the disorder, can appear suddenly or gradually and persists throughout the course of the illness. Unlike the short-term disability of an acute viral infection, for example, CFS symptoms by definition linger for at least six months and often for years (Fukuda et al., *Ann. Intern. Med* 121:953–959, 1994). Physicians can evaluate patients with persistent fatigue of undetermined cause using guidelines developed by the international CFS study group (Fukuda et al., *Fed. Pract.* 12:12–17, 1995).

Despite multidisciplinary investigations of CFS, its etiology remains unknown and no specific diagnostic tests or therapies for CFS exist. In about one third of cases, the sudden onset follows a respiratory, gastrointestinal, or other acute infection with flu-like symptoms, including mononucleosis (Mawle et al., *Infect. Agents Dis.* 2:333–341, 1994). No published data implicate a specific virus or other microbes as the cause of CFS. However, it appears that infectious agents, among other stressors, can precipitate the syndrome (National Institutes of Health Publication No. 96-484, 1996). A variety of common viruses can be reactivated in some CFS patients, including HTLV-II, Epstein-Barr virus (EBV), cytomegalovirus (CMV), herpes simplex viruses (HSV) 1 and 2, and human herpes viruses 6, 7 and 8. It is believed that virus reactivation could be occurring secondarily to some immunologic disturbance (National Institutes of Health Publication No. 96-484, 1996; Nicolson et al., *Int. J. Occup. Med. Immunol. Toxicol.* 5:69–78, 1996).

It has been well documented that individuals who suffer from fibromyalgia (FMS) exhibit many of the same symptoms found in CFS (Buchwald et al., *Arch. Intern. Med.* 154:2049–2053, 1994; Ziem et al., *Arch. Intern. Med.* 154:1913, 1995). These two illnesses are so similar that for years many medical practitioners have considered them to be the same condition. They are still regarded as closely associated with the exception of a few distinction criteria. Patients suffering from rheumatoid arthritis (RA) also exhibit certain symptoms characteristic of CFS and FMS. Although RA exhibits a narrower spectrum of clinical symptoms than the other disorders, it does exhibit a significant overlap of symptoms found in each condition.

*Mycoplasmas* are bacteria belong to the class Mollicutes. They are the smallest free-living, self-replicating bacteria known. They have no cell wall and a very limited genome of between 600 and 1,500 kilobases which makes them highly dependent on their host for survival. The *mycoplasma* species *M. fermentans*, *M. hominis* and *M. penetrans* have been isolated from individuals suffering from primary atypical pneumonia, urogenital infections, rheumatoid arthritis (RA) and AIDS-related infections (Hayes et al., *Infect. Immun.* 64:3419–3424, 1996; Schaeverbeke et al., *Br. J. Rheumatol.* 36:310–314, 1997; Montagnier et al., *Clin. Infect. Dis.* 17(Suppl. 1):S309–315, 1993).

Rapid reliable detection techniques are of great importance in a clinical diagnostic setting. Current methods of *mycoplasma* detection by culture are difficult and may take as long as five weeks to generate results which may be inconclusive or inaccurate. *Mycoplasma* may also be detected by the presence of antibodies directed against *mycoplasma* species. although this assay has a rapid turnaround time, it may lack sensitivity and specificity. Molecular methods such as DNA probes and polymerase chain reaction (PCR) techniques have also been used to detect *Mycoplasma* (Rasin et al., *Mol. Cell. Probes* 8:497–511, 1994; van Kuppeveld et al., *Appl. Environ. Microbiol.* 58:2606–2615, 1992; Hopert et al., *J. Immunol. Meth.* 164:91–100, 1993).

The practical use of PCR has been extended to multiple primer systems to meet the increased demand for multi-species detection assays (Wang et al., *Mol. Cell. Probes* 11:211–216, 1997; Kulski et al., *J. Clin. Microbiol.* 33:668–674, 1995). Multiplex PCR allows for the simultaneous detection and differentiation of multiple species with a high level of sensitivity and specificity.

There is an ongoing need for methods of identifying the three *mycoplasma* species mentioned above, and for detecting CFS infection. The present invention addresses this need.

SUMMARY OF THE INVENTION

One embodiment of the present invention is a method for determining an increased likelihood of the presence of chronic fatigue syndrome (CFS), fibromyalgia (FMS) or rheumatoid arthritis (RA) in an individual, comprising the steps of: isolating peripheral blood mononuclear cells (PBMC) from the individual; and detecting the presence of at least one *mycoplasma* species in said PBMC, wherein the presence of at least one of these species indicates an increased likelihood of the presence of CFS, FMS or RA. In one aspect of this preferred embodiment, the species is *M. fermentans*, *M. hominis* or *M. penetrans*. Preferably, the detecting step comprises a polynucleotide amplificaiton reaction. More preferably, the detecting step comprises multiplex PCR. Alternatively, the detecting step comprises Southern hybridization or dot blot hybridization. In one aspect of this preferred embodiment, the amplification reaction comprises use of two or more oligonucleotide primers selected from the group consisting of the sequences shown in SEQ ID NOS: 3–8. Preferably, the primers shown in SEQ ID NOS: 3–8. In one aspect of this preferred embodiment, the amplification reaction comprises use of two or more oligonucleotide primers having sequences shown in SEQ ID NOS: 3 and 4 so as to amplify a 206 base pair region of *M. fermentans* DNA. In another aspect of this preferred embodiment, the amplificaiton reaction comprises use of the primers having sequences shown in SEQ ID NOS: 5 and 6 so as to amplify a 170 base pair region of *M. hominis* DNA. In another aspect of this preferred embodiment, the amplification reaction comprises use of the primers having sequences shown in SEQ ID NOS: 7 and 8 so as to amplify a 407 base pair region of *M. penetrans* DNA. Preferably, the detecting step comprises detecting two or more *mycoplasma* species. Advantageously, the two or more species are selected from the group consisting of *M. fermentans, M. hominis* and *M. penetrans*. Preferably, all three of these species are detected. Preferably, the two or more species are simultaneously detected. More preferably, all three species are simultaneously detected.

DETAILED DESCRIPTION OF THE PREFERRED EMBODIMENTS

Figure 1:
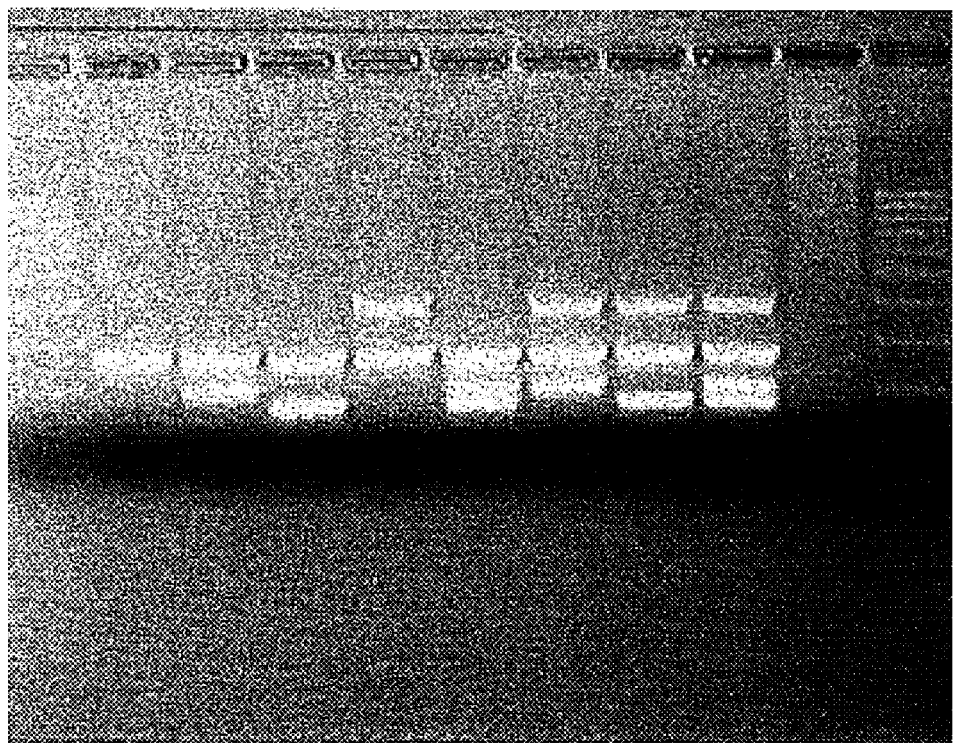
FIG. 1 is an agarose gel showing multiplex polymerase chain reaction (PCR) amplified products generated from CFS patient DNA samples. Lanes 1 and 11 are DNA size markers. Lane 2 shows a 280 bp *Mycoplasma (M.)* genus amplification product. Lane 3 shows *M.* genus and 206 bp *Mycoplasma fermentans*. Lane 4 shows *M.* genus and 170 bp *M. hominis*. Lane 5 shows *M.* genus and 470 bp *M. penetrans*. Lane 6 shows *M.* genus, *M. fermentans* and *M. hominis*. Lane 7 shows *M.* genus, *M. fermentans* and *M. penetrans*. Lane 8 shows *M.* genus, *M. hominis* and *M. penetrans*. Lane 9 shows *M.* genus, *M. fermentans, M. hominis* and *M. penetrans*. Lane 10 is a non-CFS control sample showing no *mycoplasma* infection.

The present invention provides methods for detecting an increased likelihood of the presence of CFS, FMS or RA in an individual by detecting the presence of at least one *Mycoplasma* species in PBMC from the individual. In a preferred embodiment, the *Mycoplasma* species are *M. fermentans, M. hominis* and *M. penetrans*. Although any method suitable for the detection of *Mycoplasma* species can be used, including Southern hybridization, dot blot hybridization and polynucleotide amplification, polynucleotide amplification methods are preferred. It is contemplated that any nucleic acid amplification method, preferably PCR-based amplification methods, can be used, including reverse transcriptase PCR (RT-PCR), quantitative competitive PCR (QC-PCR) and any other modified PCR, to detect the presence of *Mycoplasma* DNA or RNA. Multiplex PCR is preferred because it combines the rapidity, sensitivity, and specificity of conventional PCR with multiple species detection and differentiation, in effect alleviating the cost, reagent usage and labor of individual reactions to achieve the same result. The multiplex PCR method uses one set of oligonucleotide primers which are specific for a highly conserved region among all members of the genus *mycoplasma*, along with one or more other primer sets which are specific for various *Mycoplasma* species, such as *M. fermentans, M. hominis* and *M. penetrans*. Although amplification of a particular region specific to the genome of each of these species is exemplified below, the amplification of any genome region unique to a particular *Mycoplasama* species is within the scope of the present invention In a preferred embodiment, two or more *Mycoplasma* species are detected. In another preferred embodiment, the PCR amplification reaction uses two or more of the oligonucleotide primers in SEQ ID NOS: 3–8. In any of the embodiments discussed above, the two or more *Mycoplasma* species can be detected either separately or simultaneously.

The multiplex PCR method was applied to DNA extracted from PBMC of individuals with CFS (n=100), FMS (n=40) and RA (n=60). The percentage of M. genus infection was 52, 54, and 49%, respectively, while only 15% of healthy control individuals were infected. *M. fermentans* was detected in 32, 35, and 23%; *M. hominis* was detected in 9, 8, and 11%; and *M. penetrans* was detected in 6, 4, and 7% of CFS, FMS and RA patients, respectively. *M. fermentans, M. hominis* and *M. penetrans* were detected in 8, 3 and 2% of the healthy control subjects, respectively.

These results indicate that not only is *mycoplasma* infection occurring at a statistically significant rate in patients with CFS and related conditions over healthy controls, but also that *M. fermentans* was detected at a significantly higher rate over *M. hominis* and *M. penetrans* in each sample set. *M. fermentans* infection averaged 32% over the combined sample sets with the highest infection rate found in FMS patients (35%), and the lowest in RA patient samples (23%). *M. hominis* was detected at an average of 8% over the combined sample sets with the highest infection rate found in RA patient samples (11%), and the lowest in FMS patient samples (8%). *M. penetrans* was detected at an average of 5% over the combined sample sets, with the highest infection rate found in RA patient samples (7%), and the lowest in FMS patient samples (4%). There were *mycoplasma* infections detected by the genus-specific primer set that were not identified by the three species-specific primer sets used in this assay. This indicates that patients from each sample set are infected with other *mycoplasma* species that remain to be identified.

This assay provides a rapid and cost efficient procedure for screening cell cultures or clinical samples for the presence of three potentially pathogenic species of *mycoplasma* with a high level of sensitivity and specificity.

The present method can be combined with one or more other methods for determining an increased likelihood of the presence of CFS to increase the certainty of diagnosis thereof. Such methods include those described in U.S. Pat. Nos. 5,776,690, 5,766,859, 5,830,668, and 5,853,996, the entire contents of which are hereby incorporated by reference.

EXAMPLE 1

Cell Lines

A collection of samples from 20 different cell lines was obtained from the American Type Culture Collection (ATCC; Rockville, Md.) and different research laboratories throughout the Los Angeles area. Each sample was tested for *mycoplasma* contamination by direct agar cultivation, Hoechst stain or PCR in the facility from which the samples were obtained. If the samples were contaminated with *mycoplasma*, the causative species was identified by a series of single species PCR assays. These samples were used to determine the detection capabilities of the multiplex PCR by comparing the results of single-species PCR assays conducted by outside laboratories to the multiplex PCR described in Example 5 (Table 1) The multiplex PCR had a correlation of 100% when compared to the results of single-species PCR assays conducted by independent laboratories on the same set of samples from 20 different cell lines. (Table 1).

TABLE 1

Correlation of single-species polymerase chain reaction (PCR) with multiplex PCR on cell-line samples

| Cell line | Mycoplasma contamination | Contaminating species by PCR | Multiplex PCR M. genus | fermentans | hominis | penetrans |
|---|---|---|---|---|---|---|
| K-562 | Yes | fermentans | + | + | − | − |
| Daudi | No | | − | − | − | − |
| Raji | Yes | hominis | + | − | + | − |
| MOLT-4 | Yes | orale | + | − | − | − |
| HeLa | Yes | hominis & fermentans | + | + | + | − |
| Jiyoye | No | | − | − | − | − |
| 6T-CEM | Yes | fermentans | + | + | − | − |
| J-A1886 | Yes | hominis | + | − | + | − |
| J-111 | Yes | hominis | + | − | + | − |
| WI-1003 | Yes | pneumoniae | + | − | − | − |
| AGR-ON | Yes | fermentans | + | + | − | − |
| 6T-CEM 20 | Yes | hominis | + | − | + | − |
| H9/HTLV-IIIB | Yes | penetrans | + | − | − | + |
| T84 | Yes | fermentans | + | + | − | − |
| HCT 116 | No | | − | − | − | − |
| MOLT-3 | Yes | orale | + | − | − | − |
| CCRF-CEM | Yes | hominis | + | + | − | + |
| UACC-893 | No | | − | − | − | − |
| NC-37 | Yes | fermentans & penetrans | + | + | − | + |

Cell line samples were obtained from ATCC or outside laboratories. Each sample was tested for *mycoplasma* contamination at the facility from which they were obtained by direct agar cultivation, Hoechst stain or PCR. The contaminating species was determined by single-species PCR. The cell lines were used to assess the specificity of the multiplex PCR by correlating the results with the single-species PCR.

The optimized *mycoplasma* multiplex PCR was also found to maintain a constant detection limit when presented with varying combinations and concentrations of each *mycoplasma* species. When the multiplex PCR was applied to clinical samples, the assay was able to detect each target sequence without any cross-reaction or interference from background DNA. The amplified products from actual clinical samples which consisted of *M. penetrans* (407 bp), M. genus (280 bp), *M. fermentans* (206 bp), and *M. hominis* (170 bp) were clearly detectable when visualized by agarose gel electrophoresis (FIG. 1).

EXAMPLE 2

Clinical Specimens

A total of 100 CFS patients were chosen for this study from various clinics throughout the country. The ages of the CFS patients ranged from 25 to 62 years with a median age of 44 years. All subjects in this study met the epidemiological case definition of CFS established by the Centers for Disease Control and Prevention (CDC., Atlanta, Ga.) (Fukuda et al., *Ann. Intern. Med.* 121:953–959, 1994). At the time of evaluation and according to medical history, all patients complained of fatigue, while 80% of patients complained of exhaustion, sleep disorders, arthralgia myalgia and sore throat. Each patient had been ill for 1–5 years, and any other conditions that may cause CFS-like symptoms excluded individuals from the study. A total of 100 age- and sex-matched control subjects were chosen for this study. Each of these individuals was reported to be healthy after routine examinations. All blood samples were obtained under identical conditions to eliminate variation between samples.

EXAMPLE 3

*Mycoplasma* Strains and Culture Conditions

The different strains of each *mycoplasma* species used in the standardization of the multiplex PCR and their source is shown in Table 23.

TABLE 2

Mycoplasma species and strains used to standardize the multiplex polymerase chain reaction

| Species | Strain | Source |
|---|---|---|
| Mycoplasma fermentans | PG18 | ATCC 19989 |
| | G11 [G] | ATCC 15474 |
| Mycoplasma hominis | H34 | ATCC 15056 |
| | 132 | ATCC 43521 |
| | 183 | ATCC 43522 |
| Mycoplasma penetrans | GTU-54-6A1 | ATCC 55252 |

*M. fermentans* and *M. hominis* were grown in ATCC Culture Medium 243 MYCOPLASMA MEDIUM. *M. penetrans* was grown in ATCC Culture Medium 988 SPIROPLASMA MEDIUM SP-4. Each culturing procedure was conducted according to the specific instruction for each *mycoplasma* species provided by ATCC. Briefly, the lyophilized bacterial pellets were resuspended in their respective medium and allowed to revive under culture conditions of 37° C. and 5% $CO_2$ for 48 hours to minimize cell loss. A 10-fold serial dilution ranging from $10^{-1}$ to $10^{-8}$ was prepared from each stock culture. A volume of 0–1 ml of each of the *M. fermentans* and *M. hominis* cultures was plated on solid medium in duplicate and incubated for a period of six weeks. The colonies were counted under a microscope to determine the colony forming unit (CFU) values which were used to determine the bacterial cell count of the stock culture. The *M. penetrans* bacterial cell copy number was determined by incubating the 10-fold dilution series in 1 ml of broth at 37° C. and 5% $CO_2$ until any sign of growth could be determined. The most obvious signs of growth were broth indicator color change, any sign of sediment or turbidity when compared to an uninnoculated control tube containing only growth medium. The final dilution in the series where bacterial growth was observed was used to determine the bacterial cell count. This method was used because *M. penetrans* does not easily grow in solid medium as it is much more fastidious than *M. fermentans* and *M. hominis*.

EXAMPLE 4

DNA Isolation

Total DNA was extracted and purified using methods described by Sambrook et al. (*Molecular Cloning: a Laboratory Manual,* Cold Spring Harbor Laboratory Press, cold Spring Harbor, N.Y., 1989). Briefly, 10 ml of blood was collected in tubes containing acid citrate dextrose (ACD) solution A (Becton-Dickinson, Franklin Lakes, N.J.) gently layered over Histopaque (Sigma, St. Louis, Mo.) and centrifuged at 2,000 rpm for 30 min. PBMC were collected and washed twice with PBS, pH 7.4. DNA from PBMC and cell lines was extracted by the same method. The cells were treated with 10 mM Tris-HCl, pH 8.0, 1 mM EDTA (TE), 1% SDS containing 20 $\mu$g/ml proteinase K for 2 h at 55° C. DNA was extracted with phenol/chloroform/isoamyl alcohol (25:24:1) and precipitated with 0.1 volume of 3 M sodium acetate and 2 volumes of absolute ethanol, then incubated at −20° C. overnight. Samples were centrifuged at 14,000×g for 20 min, and the pellets were dried in a centrivap concentrator (Labconco, Kansas City, Mo.) for 12 min at 60° C. DNA pellets were resuspended in 100 $\mu$l TE. The DNA concentration and purity were determined spectrophotometrically by measuring the absorbance at 260 and 280 nm. Human genomic DNA sample concentrations were standardized at 0.2 mg/ml and stored at −20° C. until used.

EXAMPLE 5

Multiplex PCR

The four sets of oligonucleotide primers were selected based on their ability to efficiently amplify specific target sequences under the same reaction conditions. Primer set 1,5'-GGGAGCAAACAGGATTAGATACCCT-3' (SEQ ID NO: 1) and 5'-TGCACCATCTGTCACTCTGTTAACCTC-3' (SEQ ID NO: 2) are *mycoplasma* genus specific primers which amplify a 280 bp region in all species of *mycoplasma* (van Kuppeveld et al., *Appl. Environ, Microbiol.* 60149-152, 1994). Primer set 2,5'-GGACTATTGTCTAAACAATTTCCC-3' (SEQ ID NO: 3) and 5'-GGTTATTCGATTTCTAAATCGCCT-3' (SEQ ID NO: 4) specifically amplify a 206 bp region of the *M. fermentans* genome (Hawkins et al., *j. Infect. Dis.* 165581-585, 1992). Primer set 3,5'-ATACATGCATGTCGAGCGAG-3' (SEQ ID NO: 5) and 5'-CATCTTTTAGTGGCGCCTTAC-3' (SEQ ID NO: 6) are specific for a 170 bp region of the *M. hominis* genome (Grau et al., *Mol. Cell. Probes* 8139-148, 1994). Primer set 4,5'-CATGCAAGTCGGACGAAGCA-3' (SEQ ID NO: 7) and 5'-AGCATTTCCTCTTCTTACAA-3' (SEQ ID NO: 8) are specific for a 407 bp region of the *M. penetrans* genome (Grau et al; supra).

The multiplex PCR reaction components and cycling parameters were determined through a number of initial trial amplifications. Every aspect of the reaction which could affect the amplification efficiency was manipulated in different combinations to achieve optimal results, including DNA and reagent concentrations, annealing temperatures and *mycoplasma* cell copy numbers. The optimal primer concentrations were determined by experimenting with equal and staggered primer concentrations to generate equal products from each primer set. (Bej et al., *Mol. Cell. Probes* 4:353–365, 1990). The optimized reaction was carried out in a final volume of 100 $\mu$l and each reaction mixture contained 10 mM Tris-HCl, pH 8.3, 50 mM KCl, 1.5 mM $MgCl_2$, 200 $\mu$M of each dNTP, 50 pmol of each oligonucleotide primer, 2.5 units of Taq polymerase and 1 $\mu$g of DNA. The DNA amplification was performed in a GENE AMP 9600 thermal cycler (Perkin-Elmer, Norwalk, Conn.). The reaction parameters consisted an initial 3 min denaturation step at 94° C., followed by 40 amplification cycles consisting of a denaturation step at 94° C. for 45 s, an annealing step at 55° C. for 1 min and an extension step at 72° C. for 2 min. The final cycle was followed by an additional extension step at 72° C. for 10 min. A volume of 20 $\mu$l from each reaction was separated on a 1.8% agarose gel and stained with 0.5 $\mu$g/ml ethidium bromide. Amplified products were visualized under ultraviolet light.

Figure 2:
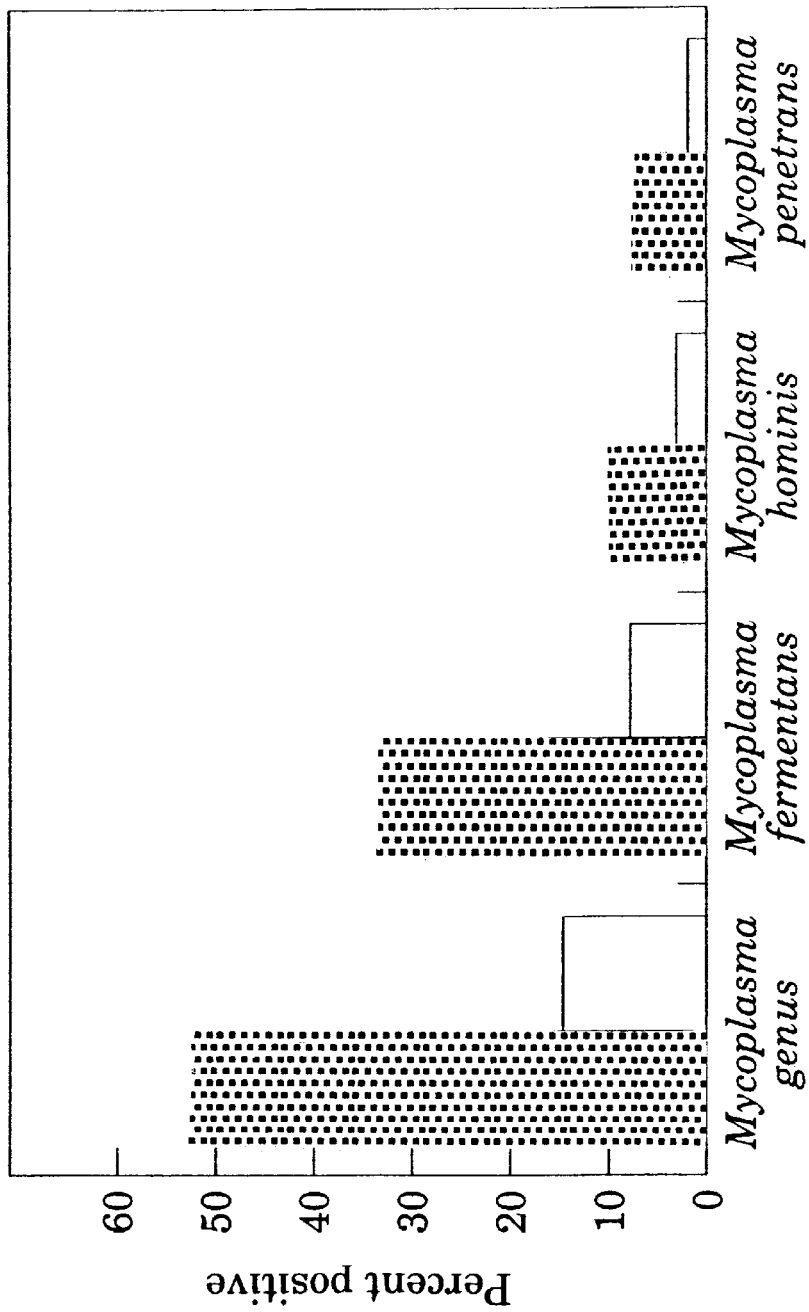
FIG. 2 is a graph showing the percentage of *mycoplasma* infections in patients with chronic fatigue syndrome (CFS). The CFS group is represented by the solid bars and the controls are represented by the open bars.

When the optimized multiplex PCR was used to detect the presence of *mycoplasmas* in patients with CFS (n=100), FMS (n=40), RA (n=60), and healthy controls (n=100), it was found that the percentage of *M.* genus infection was 52, 54, and 49%, respectively, while only 15% of healthy control individuals were infected. *M fermentans* was detected in 32, 35, and 23%; *M. hominis* was detected in 9, 8, and 11%, and *M. penetrans* was detected in 6, 4, and 7% of CFS, FMS, and RA patients, respectively. *M. fermentans, M. hominis* and *M. penetrans* were detected in 8, 3 and 2% of the healthy control subjects, respectively (Table 3; FIG. 2). These results indicate that not only is *mycoplasma* infection occurring at a statistically significant rate in CFS patients over healthy controls, but also that *M. fermentans* accounted for over half of the total *mycoplasma* infections in the CFS group. *M. fermentans* infection was 24% greater in CFS patients than in healthy matched control samples. *M. hominis* and *M. penetrans* were detected at a rate of 6 and 4% higher in the CFS group over the control group, respectively. A total of 3% of the CFS group had multiple *mycoplasma* infections of two species, and only 1% was infected with each of the three *mycoplasma* species identified by this assay. There were no multiple *mycoplasma* infections detected in the control group.

TABLE 3

Percentages of positive results from each sample group tested

| Mycoplasma | CFS | FMS | RA | Controls |
| --- | --- | --- | --- | --- |
| genus | 52 | 54 | 49 | 15 |
| fermentans | 32 | 35 | 23 | 8 |
| hominis | 9 | 8 | 11 | 3 |
| penetrans | 6 | 4 | 7 | 2 |

To determine the sensitivity of the multiplex PCR, PBMC were isolated from a healthy individual who was negative for all *mycoplasma* species by PCR. The cells were stained with 0.4% trypan blue (Sigma) and counted using a hemocytometer. Serial dilutions of the known *mycoplasma* stock cultures, which were determined by the previously described culture methods for each species, were added to equal numbers of PBMC ($1 \times 10^6$). DNA was extracted from each sample using the previously described extraction procedure and each sample was subjected to multiplex PCR. This method was used because it most accurately resembles the natural state of *mycoplasma* infected clinical samples, but it does create the possibility of generating inaccurate detection limit values. This method allows for the possibility that some non-viable *mycoplasma* cells may have been added to the negative control PBMC following the culturing procedure. These cells would have been overlooked when determining the CFU value, but still have contributed their genome to the reaction. This would alter the sensitivity level of the assay by giving a lower detection limit than was actually achieved.

A second procedure was used to confirm the detection limit results generated by the initial sensitivity level experiment. Known quantities of purified *mycoplasma* DNA were added to 1 µg of human genomic DNA and subjected to multiplex PCR. The added DNA quantities were converted into bacterial cell copy numbers using the genome size of each *mycoplasma* species. This procedure enabled greater control to be maintained over the number of DNA templates which were added to the reaction than was possible by the first method. By implementing this method, any uncertainty created by the former method was eliminated, and the multiplex PCR detection limit was confirmed for each *mycoplasma* species.

Various concentrations and combinations of *mycoplasma* cell copies of each species were also introduced into the same reaction ranging from 1 to 50 cell copies per µg of human genomic DNA. This was done to determine the ability of the multiplex PCR to detect multiple species in the same reaction and the level of sensitivity at which it does so. The lowest number of *mycoplasma* cell copies where all species were clearly visible using agarose gel electrophoresis was considered to be the detection limit for the assay.

Each *mycoplasma* species that was targeted in the assay was detectable at different bacterial cell copy numbers present amount 1 µg of human genomic DNA. The *mycoplasma* genus and *M. fermentans* primer sets had a detection limit of seven bacterial cells per µg of human DNA, whereas the *M. hominis* primer set was slightly less sensitive, with the ability to detect none *mycoplasma* cells per µg of human DNA. The *M. penetrans* primer set had the lowest sensitivity overall, with the ability to detect copies of that species in the presence of 1 µg of human genomic DNA. The bacterial cell copy number detection limits were confirmed by the use of purified *mycoplasma* DNA. There was no cross-reaction with any of the species-specific primer sets when presented with control DNA from other *mycoplasma* species. The *mycoplasma* genus primer set was able to amplify the predicted 280 bp region of each *mycoplasma* species, and did not react with any of the *non-mycoplasma* DNA controls.

The reaction specificity was checked for the possibility of cross-reactions with other *mycoplasma* species and closely related Gram-positive bacteria. The reaction fidelity was assessed by adding 100 ng of purified DNA from *M. genitalium* (ATCC 49123), *M. orale* (ATCC 23714), *M. pirum* (ATCC 25960), *M. pneumoniae* (ATCC 15531), *M. arthritidis* (ATCC 35943), *Clostridium innocuum* (ATCC 14501), *Clostridium ramosum* (ATCC 25582), *Bacillus subtilis* (ATCC 6051) and *Escherichia coli* (ATCC 11775) to the reaction mixture in the absence and presence of negative control human genomic DNA and subjecting the samples to amplification under the conditions previously described.

It should be noted that the present invention is not limited to only those embodiments described in the Detailed Description. Any embodiment that retains the spirit of the present invention should be considered to be within its scope. However, the invention is only limited by the scope of the following claims.

What is claimed is:

1. A method for determining an increased likelihood of the presence of chronic fatigue syndrome (CFS) or fibromyalgia (FMS) in an individual, comprising the steps of:
   isolating peripheral blood mononuclear cells (PBMC) from said individual; and
   detecting the presence of at least one *mycoplasma* species, wherein said at least one species comprises *M. hominis,* wherein the presence of at least one of said species indicates an increased likelihood of the presence of CFS or FMS.

2. The method of claim 1, wherein the *mycoplasma* species additionally comprises a species selected from the group consisting of *M. fermentans* and *M. penetrans.*

3. The method of claim 1, wherein said detecting step comprises a polynucleotide amplification reaction.

4. The method of claim 3, wherein said detecting step comprises multiplex PCR.

5. The method of claim 1, wherein said detecting step comprises Southern hybridization or dot blot hybridization.

6. The method of claim 3, wherein said amplification reaction comprises use of two or more oligonucleotide primers selected from the group consisting of the sequences shown in SEQ ID NOS: 3–8, wherein said two or more primers include primers having the sequences shown in SEQ ID NOS: 5 and 6 so as to amplify a 170 base pair region of *M. hominis* DNA.

7. The method of claim 6, wherein the the amplification reaction comprises use of the primers having sequences shown in SEQ ID NOS: 3 and 4 so as to amplify a 206 base pair region of *M. fermentans* DNA.

8. The method of claim 6, wherein the the amplification reaction comprises use of the primers having sequences shown in SEQ ID NOS: 7 and 8 so as to amplify a 407 base pair region of *M. penetrans* DNA.

9. The method of claim 1, wherein the detecting step comprises detecting two or more of said *mycoplasma* species.

10. The method of claim 9, wherein the two or more species comprise *M. hominis* and a species selected from the group consisting of *M. fermentans* and *M. penetrans*.

11. The method of claim 10, wherein *M. fermentans, M. hominis* and *M. penetrans* are all detected.

12. The method of claim 9, wherein the two or more species are simultaneously detected.

13. The method of claim 11, wherein *M. fermentans, M. hominis* and *M. penetrans* are detected simultaneously.

14. A method for determining an increased likelihood of the presence of rheumatoid arthritis (RA) in an individual, comprising the steps of:
  isolating peripheral blood mononuclear cells (PBMC) from said individual; and
  detecting the presence of at least one *mycoplasma* species in said PBMC, wherein the presence of at least one of said species indicates an increased likelihood of the presence of RA.

15. The method of claim 14, wherein the species detected is selected from the group consisting of *M. fermentans, M. hominis* and *M. penetrans*.

16. The method of claim 14, wherein said detecting step comprises a polynucleotide amplification reaction.

17. The method of claim 16, wherein said detecting step comprises multiplex PCR.

18. The method of claim 14, wherein said detecting step comprises Southern hybridization or dot blot hybridization.

19. The method of claim 16, wherein said amplification reaction comprises use of two or more oligonucleotide primers selected from the group consisting of the sequences shown in SEQ ID NOS: 3–8.

20. The method of claim 19, wherein the amplification reaction comprises use of the primers having sequences shown in SEQ ID NOS: 3 and 4 so as to amplify a 206 base pair region of *M. fermentans* DNA.

21. The method of claim 19, wherein the amplification reaction comprises use of the primers having sequences shown in SEQ ID NOS: 5 and 6 so as to amplify a 170 base pair region of *M. hominis* DNA.

22. The method of claim 19, wherein the amplification reaction comprises use of the primers having sequences shown in SEQ ID NOS: 7 and 8 so as to amplify a 407 base pair region of *M. penetrans* DNA.

23. The method of claim 14, wherein the detecting step comprises detecting two or more *mycoplasma* species.

24. The method of claim 23, wherein the two or more species are selected from the group consisting of *M. fermentans, M. hominis* and *M. penetrans*.

25. The method of claim 24, wherein *M. fermentans, M. hominis* and *M. penetrans* are all detected.

26. The method of claim 23, wherein the two or more species are simultaneously detected.

27. The method of claim 25, wherein *M. fermentans, M. hominis* and *M. penetrans* are detected simultaneously.

* * * * *

UNITED STATES PATENT AND TRADEMARK OFFICE
CERTIFICATE OF CORRECTION

PATENT NO. : 6,815,161 B2
DATED : November 9, 2004
INVENTOR(S) : Aristo Vojdani

It is certified that error appears in the above-identified patent and that said Letters Patent is hereby corrected as shown below:

Title page,
Item [56], References Cited, U.S. PATENT DOCUMENTS, after "5,627,275 A" insert -- * --.
OTHER PUBLICATIONS,
"Nicolson" 1st reference, after "69-78." insert -- * --.
"Nicolson" 2nd reference, after "266-271." insert -- * --.
"Ginsburg" reference, after "429-433." insert -- * --.
"Nicolson" 3rd reference, after "1:80-92." insert -- * --.
"Hawkins" reference, delete "Detction of Amplifierd" and insert -- Detection of Amplified --.
"Wang" reference, after "Cell" insert -- . --.
"Vojdani" reference, delete "et al." and insert -- et al., --.

Signed and Sealed this

Fourth Day of April, 2006

JON W. DUDAS
*Director of the United States Patent and Trademark Office*